United States Patent [19]

Del Vecchio et al.

[11] Patent Number: 4,562,287

[45] Date of Patent: Dec. 31, 1985

[54] 2-(4-BIPHENYLYL)-4-HEXENOIC ACID AND DERIVATIVES THEREOF HAVING ANTI-INFLAMMATORY ACTIVITY

[75] Inventors: Alfonso Del Vecchio; Grazia Sestini, both of Milan, Italy

[73] Assignee: Scharper S.p.A. per l'Industria Farmaceutica, Milan, Italy

[21] Appl. No.: 614,754

[22] Filed: May 29, 1984

[30] Foreign Application Priority Data

Jun. 3, 1983 [IT] Italy ................ 21456 A/83

[51] Int. Cl.$^4$ .................................... C07C 63/33
[52] U.S. Cl. .................................... 562/492; 514/532; 514/568; 544/158; 544/161; 560/102; 568/322; 568/323
[58] Field of Search ............... 562/492; 514/532, 568

[56] References Cited

U.S. PATENT DOCUMENTS 3,483,248  12/1969  Pattison ........................ 862/492

FOREIGN PATENT DOCUMENTS

| 1128851 | 5/1962 | Fed. Rep. of Germany | 562/492 |
| 612474 | 11/1960 | Italy | 562/492 |
| 616252 | 1/1961 | Italy | 562/492 |
| 616253 | 1/1961 | Italy | 562/492 |

*Primary Examiner*—Paul J. Killos
*Attorney, Agent, or Firm*—Stevens, Davis, Miller & Mosher

[57] ABSTRACT

Therapeutic compositions having anti-inflammatory and analgesic activity, containing as active compound 2-(4-biphenylyl)-4-hexenoic acid and/or derivatives thereof, characterized by low toxicity and by the absence or minimum level of ulcerogenic effect.

3 Claims, No Drawings

2-(4-BIPHENYLYL)-4-HEXENOIC ACID AND DERIVATIVES THEREOF HAVING ANTI-INFLAMMATORY ACTIVITY

This invention concerns therapeutic compositions having anti-inflammatory and analgesic activity and useful in human and veterinary therapy, comprising as active principle the 2-(4-biphenylyl)-4-hexenoic acid in its levogyre, dextrogyre and racemic form, or a derivative thereof. The active principle is defined by the following general formula:

$$X-\text{C}_6\text{H}_4-\text{C}_6\text{H}_4-\underset{\underset{CH_2-CH=CH-CH_3}{|}}{CH}-COOH$$

wherein X is H or halogen, and can be in form of a salt with a pharmacologically acceptable basic compound. Specific compounds comprised in the above general formula are the following:

1. (+) 2-(4-biphenylyl)-4-hexenoic acid (dextrogyre form) SCR 152

$$(+)\ \text{C}_6\text{H}_5-\text{C}_6\text{H}_4-\underset{\underset{CH_2-CH=CH-CH_3}{|}}{C}-COOH \qquad .\text{C}_{18}\text{H}_{18}\text{O}_2 \qquad (I)$$

2. Triethanolamine salt of dextrogyre form SCR 153

$$(+)\ \text{C}_6\text{H}_5-\text{C}_6\text{H}_4-\underset{\underset{CH_2-CH=CH-CH_3}{|}}{CH}-COOH \quad .\underset{\underset{CH_2-CH_2-OH}{|}}{\underset{|}{CH_2-CHOH}}\underset{}{N-CH_2-CH_2-OH} \qquad (II)$$

$\text{C}_{18}\text{H}_{18}\text{O}_2.\text{C}_6\text{H}_{15}\text{NO}_3$ 3. (−) 2-(4-biphenylyl)-4-hexenoic acid (levogyre form) SCR 156

$$(-)\ \text{C}_6\text{H}_5-\text{C}_6\text{H}_4-\underset{\underset{CH_2-CH=CH-CH_3}{|}}{CH}-COOH \qquad .\text{C}_{18}\text{H}_{18}\text{O}_2$$

4. 2-(4-biphenyl)-4-hexenoic acid (racemic form) or diphenesenic acid. SCR 157

$$\text{C}_6\text{H}_5-\text{C}_6\text{H}_4-\underset{\underset{CH_2-CH=CH-CH_3}{|}}{CH}-COOH \qquad .\text{C}_{18}\text{H}_{18}\text{O}_2 \qquad (III)$$

5. Chloroderivative of the racemic form. SCR 158

$$\text{Cl}-\text{C}_6\text{H}_4-\text{C}_6\text{H}_4-\underset{\underset{CH_2-CH=CH-CH_3}{|}}{CH}-COOH \qquad \text{C}_{18}\text{H}_{17}-\text{O}_2\text{Cl}$$

2-[4-biphenylyl-(4′ chloro)]4-hexenoic acid or: 4-chloro-diphenesenic acid

6. Fluoroderivative of the racemic form SCR 159

$$F-\text{C}_6\text{H}_4-\text{C}_6\text{H}_4-\underset{\underset{CH_2-CH=CH-CH_3}{|}}{CH}-COOH \qquad .\text{C}_{18}\text{H}_{17}\text{O}_2\text{F} \qquad (IV)$$

2-[4-biphenylyl-(4′ fluoro)]4-hexenoic acid or: 4-chloro-diphenesenic acid.

The drugs according to this invention administered "per os" in doses therapeutically effective, do not show ulcerogenic effects as it occurs using many drugs having anti-inflammatory activity.

Thereunder are reported laboratory tests relevant to anti-inflammatory and analgesic activity and the toxicity data. From the data and results set forth in the tables one can realize that the drugs above defined show very good values of the therapeutic index taking into account the low values of toxicity in connection with the doses required for obtaining a good therapeutic effect.

The results are shown in the following Tables, wherein are reported, for comparison purpose, also the results obtained with anti-inflammatory and analgesic drugs of the prior art. It is known from the British Patent No. 847.779 that 2-(4-biphenylyl)-4-hexenoic acid exhibits properties of anticholesterinemic and antiliphaemic agent. It was in no way obvious to foresee that said acid and its above defined derivatives could exhibit an anti-inflammatory effect, when used in proper doses, without causing side ulcerogenic effect as it occurs with many anti-inflammatory agents of the prior art, such as indomethacin, ibuprofen, oxyphenbutazone, phenylbutazone. It is possible to notice from Table 11 that the anti-inflammatory effect obtained by using 50 mg of compound SCR 153 is near equal to the one obtained with 5 mg of indomethacin with the difference that such dose of indomethacin exhibits surely ulcerogenic effect whereas it is doubtful that above dose (50 mg) of SCR 153 could have any ulcerogenic effect.

Furthermore in the case of compound SCR 152 one can notice a rather good anti-inflammatory effect at dose of 50 mg whereas the same dose exhibits none ulcerogenic effect.

The tests relevant to the toxicity and to the anti-inflammatory and analgesic activity are summarized in the following Tables.

TABLE 1

| | TOXICITY | | |
|---|---|---|---|
| Drug | Animal | Way | DL$_{50}$ mg/Kg |
| SCR 153 | mouse | i.p. | 315 (274–362) |
| SCR 152 | mouse | p.o. | 1550 (1370–1750) |
| SCR 152 | rat | p.o. | 1350 (1140–1590) |
| SCR 153 | mouse | p.o. | 1056 (934–1193) |
| SCR 153 | rat | p.o. | 640 (537–761) |
| SCR 158 | rat | p.o. | 940 (870–1015) |
| SCR 159 | rat | p.o. | 900 (750–1098) |
| SCR 157 | rat | p.o. | 1000 (885–1113) |
| SCR 157 | mouse | p.o. | 1100 (802–1507) |

TABLE 2

| ANTI-INFLAMMATORY ACTIVITY. Carragenine induced edema, first test. | | | |
|---|---|---|---|
| Drug | Dose in mg/Kg p.o. | % inhibition | Correlation coefficient |
| SCR 153 | 12.5 | 24 | 0.985 |
| | 25 | 29 | |
| | 50 | 45 | |
| | 100 | 53 | |

TABLE 2-continued

ANTI-INFLAMMATORY ACTIVITY.
Carragenine induced edema, first test.

| Drug | Dose in mg/Kg p.o. | % inhibition | Correlation coefficient |
|---|---|---|---|
| IBUPROFEN | 12.5 | 27 | 0.987 |
|  | 25 | 33 |  |
|  | 50 | 47 |  |
|  | 100 | 54 |  |
| INDOMETHACIN | 2.5 | 33 | 0.947 |
|  | 5 | 36 |  |
|  | 10 | 48 |  |
| PHENYL-BUTAZONE | 75 | 43 | 0.974 |
|  | 150 | 46 |  |
|  | 300 | 153 |  |

TABLE 3

Edema induced by different substances.

| | | % edema inhibition | | | | |
|---|---|---|---|---|---|---|
| Drug | Dose mg/Kg p.o. | Carragenine | Kaolin | Yeast | Serotonin | Dextrose |
| PHENYL-BUTAZONE | 50 | 13 | 41 | 7 | 24 | 0 |
|  | 100 | 32 | 40 | 23 | 12 | 0 |
|  | 200 | 61 | 53 | 18 | 25 | 18 |
| SCR 157 | 50 | 8 | 42 | 11 | 0 | 0 |
|  | 100 | 43 | 49 | 22 | 16 | 8 |
|  | 200 | 64 | 57 | 28 | 22 | 8 |
| SCR 152 | 50 | 54 | 19 | 13 | 3 | 12 |
|  | 100 | 52 | 40 | 25 | 3 | 39 |
|  | 200 | 66 | 40 | 17 | 17 | 45 |
| SCR 156 | 50 | 9 | 32 | 13 | 0 | 14 |
|  | 100 | 31 | 26 | 5 | 13 | 5 |
|  | 200 | 23 | 28 | 7 | 0 | 12 |

TABLE 4

Effect on the capillary permeability

| | ⌀ m.micron | | |
|---|---|---|---|
|  | Serotonin | Histamine | Dextran |
| Checks | 18.16 | 21.33 | 14.83 |
| SCR 157 200 mg/Kg p.o. | 16.57 | 20.28 | 14.85 |
| SCR 152 200 mg/Kg p.o. | 17.71 | 21.57 | 8.00 |
| SCR 156 200 mg/Kg p.o. | 16.43 | 21.00 | 13.58 |

TABLE 5

Cotton-pellets induced granuloma.

| | Doses | % Inhibition |
|---|---|---|
| Checks | — | — |
| Oxyphenbutazone | 200 mg/Kg p.o. | 24 |
| SCR 157 | 200 mg/Kg p.o. | 29 |
| SCR 156 | 200 mg/Kg p.o. | 11 |
| SCR 152 | 200 mg/Kg p.o. | 12 |

TABLE 6

SCR 153 activity on Freund's adjuvant induced arthritis.
Edema inhibition %

| Drug | Dose mg/Kg p.o. | 2 | 4 | 8 | 12 | 16 | 20 | 24 |
|---|---|---|---|---|---|---|---|---|
| | | Treatment time in days | | | | | | |
| SCR 153 | 40 | 60% | 40% | 56% | 61% | 59% | 56% | 55% |
| SCR 153 | 20 | 40% | 24% | 52% | 49% | 30% | 22% | 10% |
| Ibuprofen | 40 | 32% | 17% | 26% | 19% | 27% | 19% | 9% |
| Ibuprofen | 20 | 34% | 29% | 19% | 24% | 14% | — | 4% |
| Indomethacin | 2 | 49% | 35% | 51% | 48% | 71% | 73% | 71% |
| Indomethacin | 1 | 49% | 7% | 27% | 58% | 60% | 37% | 57% |

TABLE 7

Joint's diameter.

| Drug | Dose mg/Kg p.o. | 1 | 2 | 3 | 4 |
|---|---|---|---|---|---|
| | | Treatment time in weeks | | | |
| Arthritis checks | — | 0.48 | 0.71 | 0.81 | 0.85 |
| Arthritis checks | — | 0.38 | 0.75 | 0.79 | 0.89 |
| SCR 153 | 40 | 0.24 | 0.39 | 0.44 | 0.52 |
| SCR 153 | 20 | 0.46 | 0.61 | 0.62 | 0.73 |
| Ibuprofen | 40 | 0.35 | 0.60 | 0.75 | 0.80 |
| Ibuprofen | 20 | 0.31 | 0.53 | 0.65 | 0.81 |
| Indomethacin | 2 | 0.22 | 0.39 | 0.34 | 0.34 |
| Indomethacin | 1 | 0.38 | 0.50 | 0.49 | 0.55 |

TABLE 8

SH Groups in serum and erytrocytes sedimetation rate (ESR)

| Drug | Dose mg/Kg p.o. | SH groups diminution in % | E.S.R. |
|---|---|---|---|
| Arthritis checks | — | 70 | 41 |
| Arthritis checks | — | 77 | 56 |
| SCR 153 | 40 | 48 | 32 |
| SCR 153 | 20 | 79 | 59 |
| Ibuprofen | 40 | 73 | 30 |
| Ibuprofen | 20 | 78 | 58 |
| Indomethacin | 2 | 50 | 15 |
| Indomethacin | 1 | 78 | 38 |

TABLE 9

Activity on carragenine induced edema.

| Drug | Dose mg/Kg p.o. | Inhibition % |
|---|---|---|
| SCR 157 | 50 | 10 |
| " | 75 | 31 |
| " | 112,5 | 24 |
| SCR 159 | 53 | 29 |
| " | 80 | 26 |
| " | 120 | 26 |
| SCR 158 | 56 | 0 |
| " | 85 | 16 |
| " | 127 | 14 |

TABLE 10

Analgesic activity

| Drug | Dose mg/Kg p.o. | endurance time at 52° C. over checks | |
|---|---|---|---|
| | | 1 hour | 2 hours |
| | | Hot plate (I) | |
| SCR 157 | 50 | 3 | 26 |
| SCR 159 | 50 | 3 | 38 |
| " | 50 | 0 | 38 |
| | | Hot plate (II) | |
| SCR 159 | 35,6 | 22 | 43 |
| " | 53,45 | 45 | 29 |
| " | 80,18 | 26 | — |
| | | RANDALL-SELLITO pain threshold over checks | |
| SCR 159 | 23,7 | 55 | 7 |
| " | 35,6 | 49 | 32 |
| " | 53,45 | 47 | 16 |

TABLE 11

Anti-inflammatory activity on carragenine induced edema.

| Drug | Dose mg/Kg p.o. | % inhibition |
|---|---|---|
| SCR 157 | 50 | 33 |
| SCR 152 | 50 | 31 |
| SCR 153 | 50 | 37 |
| SCR 159 | 50 | 32 |

TABLE 11-continued

Anti-inflammatory activity on carragenine induced edema.

| Drug | Dose mg/Kg p.o. | % inhibition |
|---|---|---|
| Oxyphenbutazone | 50 | 41 |
| Ibuprofen | 50 | 40 |
| Indomethacin | 5 | 38 |
| Acetylsalicylic acid | 50 | 23 |

Preparation of halogen-derivatives of diphenesenic acid

The process for preparing these derivatives comprises the following steps:

1° Step:

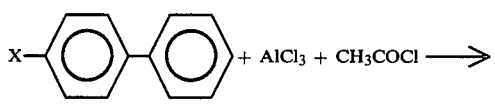

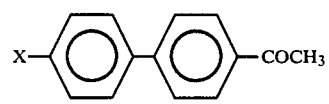

X = halogen
The reaction is carried out in inert organic solvent for example ClCH$_2$—CH$_2$Cl.

The reaction occurs in about 4 hours at 50° C. The product 4-[(4' halogen) phenyl]-acetophenone is separated from reaction mixture through conventional method and working conditions.

2° Step:

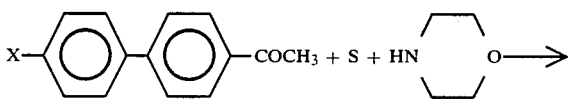

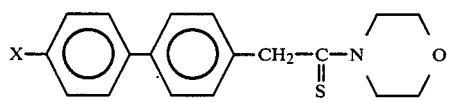

The reactants are mixed together and heated to reflux for about 5 hours. The product is recovered from reaction mixture by crystallization according to conventional method.

3° Step:

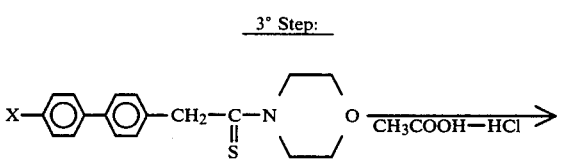

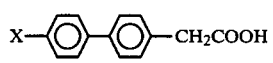

The reaction is carried out in an excess of CH$_3$COOH which acts also as reaction solvent. The reaction occurs in several hours at the boiling temperature.

The product: 4-biphenyl(4' halogen)-acetic acid is separated from by-products through conventional method and working conditions.

4° Step:

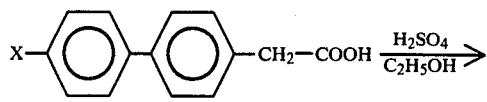

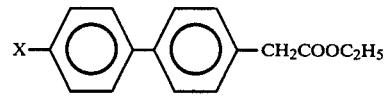

The reaction occurs according to the conventional working conditions for esterification process.

The obtained ester is a solid product which is separated from reaction mixture after dilution with water.

5° Step:

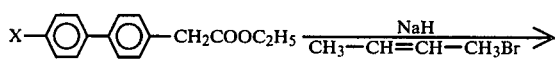

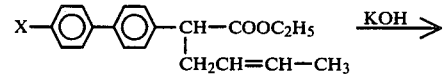

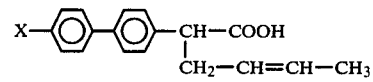

The first reaction occurs in inert solvent such as benzene at the boiling temperature of the solution, in about 2 hours. The hydrolysis of the ester intermediate occurs in conventional working conditions for ester hydrolysis. The raw product is purified through crystallization from cyclohexane.

Preparation of optical isomers of 2-(4-biphenylyl)-4-hexenoic acid (diphenesenic acid)

The separation of optical isomers starting from the racemic form is carried out through salification of the acid with an organic base which is optically active in particular quinine. The method is based on the different solubilities in ethanol of the quinine salts of the two optical isomers. Detailed report about the working conditions is set forth in Example 3.

EXAMPLE 1

Preparation of: 2-[4-biphenylyl-(4' fluoro)]-4-hexenoic acid or: 4-fluoro-diphenesenic acid

First step

In a 1 l flask were placed ml 315 of 1,2-dichloroethane, g 66,5 of AlCl$_3$ and g 34 of acetyl chloride. A poorly exothermic reaction occurs.

The reaction mixture is cooled to 10° C.

Then g 75 of 4-fluoro-biphenyl are loaded in little charge during 3 hours, avoiding to arise temperature over 20° C. The mixture is slowly heated to 50° C. and kept at this temperature for 4 hours.

The obtained solution is then poured in a mixture of g 500 ice and ml 150 of HCl 37%, under stirring. Thereafter the mixture is let to stay for 12 hours and phases decantation occurs.

Aqueous phase is extracted with 50 ml dichloroethane. Organic phases collected together are washed with H₂O (ml 250×2).

Organic phase is dried on CaCl₂ and then evaporated under vacuum till dryness.

Solid residue is warm dissolved in 80 ml acetone, then is cooled and kept under stirring 1 night. Thereafter it is let to stay 2 hours in refrigerator and then the mixture is filtered, the solid is washed with ml 15 acetone and then with ml 25 petroleum ether.

The product is dried under vacuum at 40° C.

Obtained product: 4-[phenyl-(4' fluoro)]-acetophenone: g 77, yield 83%.

Melting point 85°÷87° C.

Second step g 75 of intermediate compound obtained in first step were placed in a 500 ml flask together with ml 140 morpholine and g 22,5 sulphur and the mixture heated under reflux for 5 hours and a dark red solution was obtained.

After cooling to 50° C. and addition of ml 450 CH₃OH a solid precipitated. The mixture is kept under stirring at 50° C. for 1 hour, and then let to stay 1 night in a refrigerator. Solid product is filtered and washed with 150 ml of CH₃OH and then dried under vacuum at 50° C.

Obtained product: 4-fluoro-biphenylyl-aceto-thiomorpholinamide: g 102, yield 92%, melting point 140°÷143° C.

Third step g 102 of intermediate compound of second step were placed together with ml 166 H₂O, ml 408 CH₃COOH and 65 ml HCl 37% in a 1 l flask. The mixture is heated under reflux for 8 hours and then poured in 750 ml H₂O. The mixture is cooled to 10° C. and then filtered, the solid product is pressed and washed with 500 ml H₂O. The solid product is dispersed in 1500 ml H₂O and NaOH 30% is added to the solution till pH value arises to 9.

Sulphur is then separated through filtration and the filtered solution is heated to 60° C., decolorized with active carbon, acidified to pH 2 with HCl 10%. The solid product then separated is filtered, washed with H₂O till pH neutral. The product is then dried under vacuum at 60° C. Obtained product: 4-[biphenylyl (4' fluoro)]-acetic acid: g 45, yield 61%, melting point 133°÷134° C.

Fourth step

In a ml 500 flask there were placed ml 273 of anhydrous ethanol, ml 4 concentrated H₂SO₄ and g 41 of intermediate compound of step 3.

The mixture is heated under reflux for 3 hours.

The reaction mixture is then poured in a solution of g 25 NaHCO₃ in ml 500 of frozen water, under stirring.

Ester derivative precipitates and is filtered after 3 hours stirring.

Solid product is washed with H₂O till washing liquid is neutral.

Drying is carried out at 35° C. under vacuum.

Obtained product: ethyl-4-fluoro-biphenyl-acetate: g 45, yield 98%, melting point 60,5°÷62° C.

Fiveth step

(a) Alkylation

In a 500 ml flask there are charged g 8.5 sodium hydride titre 80% and ml 210 benzene.

Keeping temperature between 20° and 30° C. a solution of 42 g of intermediate compound of step 4 and of g 21 crotyl bromide in ml 84 of dimethylformamide is dropped during 30 minutes in the flask.

Then the reaction mixture is heated under reflux for 2 hours, and subsequently cooled to 10° C.

Thereafter ml 225 H₂O are charged and mixture stirred 15 minutes. Two phases separate.

Organic phase is washed with 100 ml H₂O and dried on Na₂SO₄. The dried solution is concentrated under vacuum till an oily residue consisting of ethyl ester of fluorodiphenesenic acid.

(b) Hydrolysis

The oily residue is dissolved in 80 ml ethanol. 95 ml H₂O and 27 g KOH are then added and the mixture is heated under reflux for 2 hours.

The alcohol is evaporated under vacuum. The residue is dissolved in 400 ml H₂O. Aqueous solution is washed with 80 ml petroleum ether. The solution is then decolorized with active carbon and acidified slowly with HCl 10% till pH 2.1. After stirring at room temperature for 4 hours the solid product is filtered, washed with H₂O till washing liquid is neutral. The solution is then dried under vacuum at 50° C. The obtained raw product (30 g) is crystallized from cyclohexane (1 volume).

Obtained product: 4-fluoro-diphenesenic acid: g 18, yield 42%, melting point 99°÷100° C.

Purity:

99.1% (acidimetric titre)

99.4% (iodine value)

EXAMPLE 2

Preparation of: 2-[4-biphenylyl-(4' chloro)]-4 hexenoic acid or: 4-chloro-diphenesenic acid.

Starting from 4-chloro-biphenyl and under the same working condition, described in the preceding example, for the fluoro derivative, 4-chloro-diphenesenic acid was obtained, having melting point 123.5°÷125° C.

Purity:

99.3%(acidimetric titre)

99.6%(iodine value)

EXAMPLE 3

Optical isomers of 2-(4-biphenylyl)-4-hexenoic acid. (diphenesenic acid)

1° Step

In a 2 l flask g 122 of quinine were dissolved in ml 1375 of ethanol, then the solution is heated to 70° C. and g 100 of diphenesenic acid are added therein; under stirring the mixture is kept at 70° C. till complete dissolution and then the warm solution is poured in a glass and let to stand in order to obtain spontaneous crystallization of the salt (+). The mixture is filtered at 30° C., the precipitate is washed with ml 125 of ethanol, the solid is dried in oven under vacuum at 90° C. Mother liquor containing the (−) salt is treated separately.

Salt obtained: g 119, (theoretical amount g 112) melting point 168°÷171° C.

The product is crystallized from 900 ml of ethanol with 1% of active carbon, then the liquid is warm filtered on heated funnel and then let to crystallize at rest: the liquid is then filtered at 30° C., the precipitate is washed with 100 ml of ethanol. The solid is dried under vacuum in oven at 90° C. Mother liquor is gathered together with precipitation liquid.

Obtained product g 85 (theoretical value g 112): yield=76%) Melting point 174°÷175° C.

Purity: 99.6%.

2° Step

In a 2 l flask fitted with stirrer, reflux condenser dipping pipe for inlet of gaseous HCl, g 79 of (+) salt are mixed with ml 1100 of anhydrous ethyl ether and under stirring anhydrous gaseous HCl is fed till pH reaches strong acid value (2÷3).

At this moment the gas fed is stopped and the reaction mixture is kept under stirring for further 30 minutes. The mixture is filtered, the precipitate (quinine hydrochloride) is washed with anhydrous ether: the filtrate and washing ether containing (+) diphenesenic acid are extracted with water after alkalinization with NaOH 10% solution. Three extractions are carried out with 200 ml water each time. Aqueous phase degassed under vacuum is acidified with 10% HCl in such way to precipitate (+) acid. Mixture is filtered on buckner funnel, the precipitate is thoroughly washed with water till neutralization of the washing liquid and disappearance of Cl−; finally the product is dried under vacuum at 70° C.

Obtained product: g 30, yield 84.3%.
Melting point 117°÷121° C.
Purity 99.86%.
$[\alpha]_D^{20} = +98°$ (C=2% in dioxane).

3° Step

Mother liquor from the filtration of (+) salt together with crystallization liquid is evaporated till very little volume, under vacuum. The optically (−) salt of quinine with diphenesenic acid precipitates.

The solid product is treated with HCl as described in Step 2, in order to recover the (−) 2-(4-biphenylyl)-4-hexenoic acid.

Obtained product: g 34 yield 64.8%.
Melting point 108°÷110° C.
$[\alpha]_D^{20} = -41.5°$ (c=1% in dioxane).

We claim:

1. Process for preparing compounds of general formula:

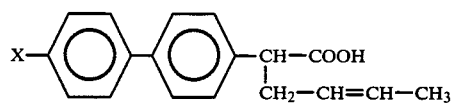

wherein X is hydrogen or fluorine or chlorine, which comprises the following process steps:

(a) reacting the diphenyl compound

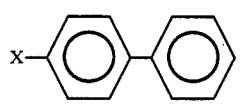

with AlCl₃ and acetyl chloride CH₃COCl, in inert organic solvent, at temperature between 20° and 50° C., obtaining the corresponding acetophenonic compound:

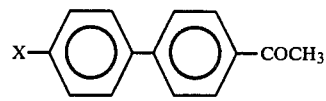

(b) the acetophenonic compound is reacted with sulphur and morpholine at reflux temperature of the reaction mixture, according to the scheme:

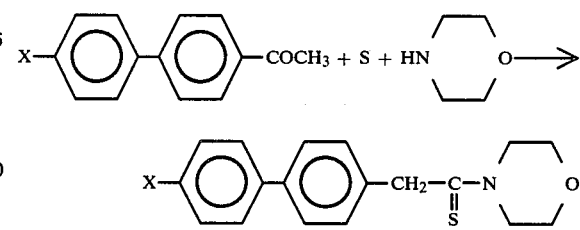

(c) the above intermediate compound is reacted with an excess of acetic acid in presence of HCl at the boiling temperature of the reaction mixture, obtaining the corresponding 4-biphenyl-acetic acid of formula

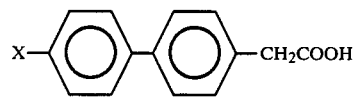

(d) the above intermediate compound is converted by conventional method (C₂H₅OH+H₂SO₄) in the corresponding ethyl ester which is reacted with BrCH₂—CH=CH—CH₃ in presence of NaH, in inert solvent, at the boiling temperature of the reaction mixture, wherein the ester of formula:

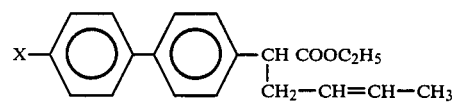

is obtained;

(e) the above intermediate ester is hydrolysed by treatment in aqueous solution of alkaline hydroxide, at boiling temperature of the mixture, wherein the final product is obtained.

2. Therapeutic method for analgesic and anti-inflammatory treatment, characterized in that a therapeutically active amount of a compound of formula:

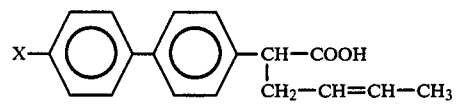

wherein X is hydrogen or chlorine or fluorine, or a salt of the same compound with a pharmacologically acceptable basic compound, is administered "per os".

3. Therapeutic method of claim 1, wherein the triethanolamine salt of the active compound is used.

* * * * *